United States Patent [19]
Reichelt et al.

[11] 4,260,601
[45] Apr. 7, 1981

[54] CHEMICAL COMPOUNDS

[75] Inventors: Karl-Ludwig Reichelt; Olav E. Trygstad, both of Oslo, Norway

[73] Assignee: Nyegaard & Co. A/S, Oslo, Norway

[21] Appl. No.: 87,525

[22] Filed: Oct. 23, 1979

Related U.S. Application Data

[63] Continuation of Ser. No. 940,018, Sep. 6, 1978.

[51] Int. Cl.$^3$ .................... A61K 37/00; C07C 103/52
[52] U.S. Cl. ............................ 424/177; 260/112.5 R; 260/112.5 TR
[58] Field of Search ................. 424/177; 260/112.5 R, 260/112.5 TR

[56] References Cited

FOREIGN PATENT DOCUMENTS 2406546  8/1975  Fed. Rep. of Germany ........... 424/177
1362023  7/1971  United Kingdom ..................... 424/177

OTHER PUBLICATIONS

Bowers, et al., Biochem. and Biophys. Res. Commun. 40, (1970) 683–691.
Sievertsson, et al., Acta Pharm. Succica, 11, 67–76, (1974).
Chang, et al., J. Med. Chem., (1971) 14, 485–487.

*Primary Examiner*—Delbert R. Phillips
*Attorney, Agent, or Firm*—Bacon & Thomas

[57] ABSTRACT

The tripeptide L-pyroglutamyl-L-histidyl-glycine is disclosed. The tripeptide possesses anorexic properties. Process for the preparation of the compound and pharmaceutical compositions containing the compound as active ingredient are described and exemplified.

9 Claims, No Drawings

CHEMICAL COMPOUNDS

This is a continuation of application Ser. No. 940,018, filed Sept. 6, 1978.

The present invention relates to a novel peptide and the salts thereof as well as to processes for their preparation. The peptide possesses interesting anorexigenic properties.

The present invention is based upon the discovery of a novel peptide found in the urine of patients suffering from severe anorexia, which peptide possesses interesting anorexigenic properties and is thus of potential interest for use against obesity caused by overeating.

Thus according to one feature of the present invention there is provided L-(pyro)glutamyl-L-histidyl-glycine and salts thereof.

The chemical formula of the novel tripeptide of the present invention is thus:

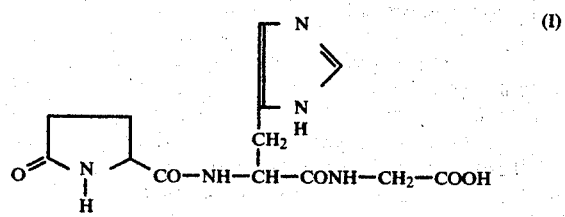

the pyroglutamyl and histidyl moieties being of the L-series.

The salts useful for incorporation in pharmaceutical compositions are the physiologically compatible salts. Other salts may however be useful in the preparation of the novel tripeptide and the physiologically compatible salts thereof.

According to a further feature of the present invention there is provided a process for the preparation of L-(pyro)glutamyl-L-histidyl-glycine which comprises deprotecting a compound of the formula:

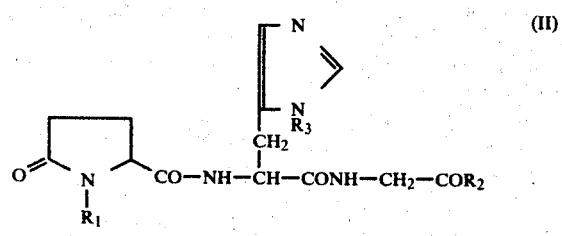

(wherein the pyroglutamyl and histidyl moieties are each of the L-series, each of $R_1$ and $R_3$ respresents a hydrogen atom or an amino protecting group and $R_2$ represents a hydroxyl group or a carboxyl protecting group with the proviso that at least one of $R_1$, $R_2$ and $R_3$ represents a protecting group) whereby L-(pyro)-glutamyl-L-histidyl-glycine or a salt thereof is obtained.

As indicated, the compound of formula II may be only partially protected, only one or two of $R_1$, $R_2$ and $R_3$ then being in protected form; such compounds may be prepared by selective partial deprotection of a compound of formula II in which all of $R_1$, $R_2$ and $R_3$ are in protected form or they may be synthesised in partially protected form. In particular, $R_3$ will commonly be hydrogen.

Where, however, a compound of formula II is used in which $R_1$, $R_2$ and $R_3$ each represent a protecting group it is advantageous to remove all the protecting groups simultaneously.

A compound of formula I or a compound of formula II may, for example, be prepared by reacting a compound of the formula:

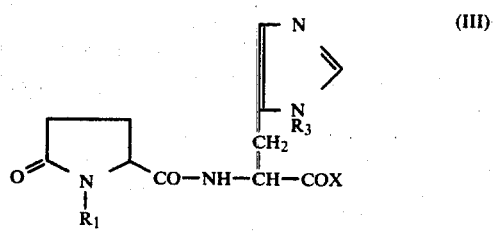

(wherein the pyroglutamyl and histidyl moieties are each of the L-series, each of $R_1$ and $R_3$ represents a hydrogen atom or an amine protecting group and X represents a hydroxyl group or a carboxylic acid activating group) with a compound of the formula:

$$NH_2-CH_2-COR_2 \qquad (IV)$$

(wherein $R_2$ represents a hydroxyl group or a carboxyl protecting group) whereby a compound of formula I or II is obtained.

A compound of formula III is preferably used in which $R_1$ represents an amine protecting group and/or X represents a carboxylic acid activating group. $R_3$ is preferably hydrogen. A compound of formula IV is preferably used in which $R_2$ represents a carboxyl protecting group.

Similarly a compound of formula I or a compound of formula II may, for example, be prepared by reacting the L-isomer of a compound of the formula:

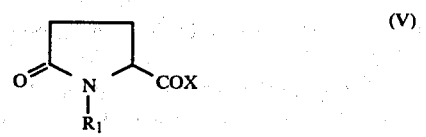

(wherein $R_1$ represents a hydrogen atom or an amine protecting group and X represents a hydroxyl group or a carboxylic acid activating group) with the L-isomer of a compound of the formula:

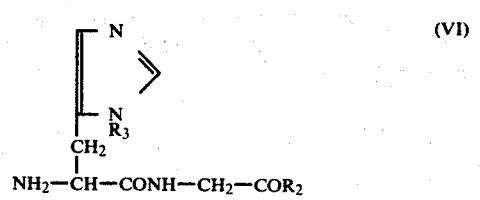

(wherein $R_2$ represents a hydroxyl group or a carboxyl protecting group and $R_3$ represents hydrogen or an amine protecting group) whereby a compound of formula I or II is obtained.

A compound of formula V is preferably used in which $R_1$ represents an amine protecting group and/or X represents a carboxyl acid activating group. $R_3$ is preferably hydrogen. A compound of formula VI is preferably used in which $R_2$ represents a carboxyl protecting group.

A compound of formula III as hereinbefore defined (wherein X represents a carboxylic acid activating group) may, for example, be prepared by reacting the L-isomer of a compound of formula III (wherein X represents a hydroxyl group) by methods known per se to form a compound of formula III wherein X represents a carboxylic acid activating group.

A compound of formula III as hereinbefore defined (wherein X represents a hydroxyl group) may, for example, be prepared by reacting the L-isomer of a compound of the formula:

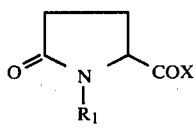

(V)

(wherein $R_1$ represents a hydrogen atom or an amine protecting group and X represents a hydroxyl group or a carboxylic acid activating group) with the L-isomer of a compound of the formula:

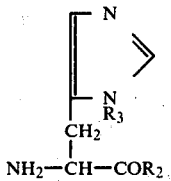

(VII)

(wherein $R_2$ and $R_3$ have the above meanings) and where a compound of formula VII is used in which $R_2$ represents a carboxyl protecting group converting the compound thus obtained into a compound of formula III (wherein X represents a hydroxyl group) by deprotection of the carboxyl protecting group.

It is preferred to use a compound of formula V in which $R_1$ represents an amine protecting group and/or in which X represents a carboxylic acid activating group. It is also preferred to use a compound of formula VII in which $R_2$ represents a carboxylic acid protecting group, which group is then removed after the reaction to form a compound of formula III in which X represents a hydroxyl group.

A compound of formula VI as hereinbefore defined may for example be prepared by removal of the amine protecting group or groups from a compound of the formula:

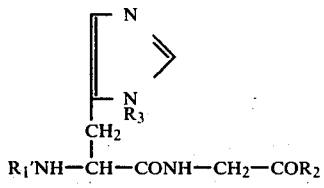

(VIa)

(wherein $R_1'$ represents an amine protecting group and $R_3$ represents hydrogen or an amine protecting group) whereby a compound of formula VI is obtained.

The compound of formula VI or VIa may, for example, be prepared by reacting the L-isomer of a compound of formula:

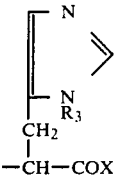

(VIII)

(wherein $R_1$ and $R_3$ have the above meanings and X represents a hydroxyl group or a carboxylic acid activating group) with a compound of the formula:

$$NH_2-CH_2-COR_2 \qquad (IV)$$

(wherein $R_2$ represents a hydroxyl group or a carboxyl protecting group) whereby a compound of formula VI or VIa is obtained.

It is preferred to use a compound of formula VIII in which $R_1$ represents an amine protecting group, which group is removed after the reaction. It is also preferred to use a compound of formula VIII in which X represents a carboxylic acid activating group. A compound of formula IV is preferably used in which $R_2$ represents a carboxyl protecting group. $R_3$ is preferably hydrogen.

Where in any of the above reactions a mixture of products is obtained the desired product may be isolated from the reaction mixture by conventional methods known per se.

It will be appreciated that the compounds of the present invention may, if desired, be prepared according to the processes herein described using the solid-phase method of peptide synthesis. In such a method the carboxyl protecting group of the C-terminal amino acid may be in the form of a resin.

The compounds of formula IV, V, VII and VIII are either readily available starting materials or may readily be derived from available starting material according to methods well known in the literature.

A wide choice of protecting and activating groups as well as procedures for protecting, activating and coupling amino acids are known and are exemplified in Schroder, E., and Lubke, K., The Peptides Vols 1 or 2, Academic Press, New York and London, 1965 and 1966; Pettit, G. R., Synthetic Peptides, Vols 1-4, Van Nostrand, Reinhold, N.Y. 1970, 1971, 1975 and 1976; Houben-Weyl, Methoden der Organischen Chemie, Synthese von Peptiden, Band 15, Georg Thiene Verlag, Stuttgart 1974; and Amino Acids, Peptides and Proteins, Vol 4-8, The Chemical Society, London 1972, 1974, 1975 and 1976.

Thus, for example amine protecting groups which may be employed include the carbobenzoxy (hereinafter also designated Cbz or Z), t-butoxycarbonyl (hereinafter also designated BOC) and acyl groups such as, for example, an acetyl group or a formyl group.

Carboxyl protecting groups which may, for example be employed include readily cleaved ester groups such as benzyl (hereinafter also designated Bzl), p-nitrobenzyl or t-butyl groups.

Carboxylic acid activating groups which may, for example, be employed include mixed anhydrides, azides or activated esters such as for example the p-nitrophenyl ester, a 2,4,5-trichlorophenyl ester, or an N-hydroxysuccinimidyl ester.

It will be appreciated that a wide range of other such groups exist as, for example, detailed in the above-mentioned literature references and the use of all such groups in the hereinbefore described processes fall within the scope of the present invention.

The processes of the present invention will generally be effected by the use of L-pyroglutamyl and L-histidyl starting materials in the absence of the D-isomers thereof. It is thus desirable to conduct the reactions under conditions which avoid racemisation in order to avoid the need for a resolution process at the end of the total reaction sequence.

It is also possible, but less convenient, to use racemic pyroglutamyl and histidyl starting materials and include one or more optical resolution stages.

Carboxyl protecting groups may be introduced by conventional methods e.g. by reaction with a suitable esterifying reagent, for example an alcohol such as benzyl or p-nitrobenzyl alcohol in the presence of acid, e.g. p-toluenesulphonic acid.

Amine protecting groups may be introduced by conventional methods e.g. by reaction with suitable acid halides such as carbobenzoxyl chloride or pivaloyl chloride, or acid anhydrides such as acetic anhydride.

In general it is convenient to effect the coupling reactions at low temperatures, for example, −20° C. up to ambient temperature conveniently in a suitable solvent system, for example, tetrahydrofuran, dioxan, dimethylformamide, methylene chloride or a mixture of these solvents.

The couplings of free amino and carboxyl groups may, for example, be effected using dicyclohexylcarbodiimide (DCC). Another coupling agent which may, for example, be employed is N-ethoxycarboxyl-2-ethoxy-1,2-dihydroquinoline.

Activation of carboxyl groups may for example be effected by conversion of the acid to a reactive derivative e.g. the acid anhydride which may for example be prepared by the use of ethyl or isobutyl chloroformate. Acylation of another amino acid with a mixed anhydride or other activated carboxyl derivative may be effected by methods conventional in the peptide synthesis.

Usually, the reaction product after the coupling step contains one or more protecting group(s). If desirable, these can be removed, for example in a selective way. Thus it is possible to remove only certain groups, keeping others intact during the subsequent reaction(s).

As stated above a wide range of procedures exist for removing amine protecting groups and carboxyl protecting groups. Thus, for example an amine protecting group may be removed by acidolysis, hydrogenolysis, treatment with dilute ammonium hydroxide, treatment with sodium, treatment with sodium amide, treatment with hydrazine, or enzymatic hydrolysis with, for example, leucineaminopeptidase. Methods which are of interest also include treatment with anhydrous hydrogen bromide for example in glacial acetic acid, treatment with trifluoroacetic acid and catalytic hydrogenation.

Thus carbobenzoxy and t-butoxy carbonyl groups may be removed, for example, using anhydrous hydrogen bromide conveniently in the presence of glacial acetic acid or using trifluoroacetic acid conveniently in the presence of concentrated hydrochloric acid; acyl groups may for example be removed by conventional hydrolysis with acid or by enzymic hydrolysis as described above.

The removal of carboxyl protecting groups may, for example, be effected by saponification, acidolysis, hydrogenolysis or enzymatic hydrolysis. Thus, for example, saponification may be effected with an alkali metal hydroxide conveniently in the presence of water, an alcohol and/or acetone. Acidolysis may, for example, be effected by the use of anhydrous hydrogen bromide or trifluoroacetic acid and hydrogenolysis may, for example, be effected by catalytic hydrogenation e.g. by the use of palladium on carbon conveniently 10% palladium on charcoal. Enzymatic hydrolysis may, for example, be effected by the use of leucineaminopeptidase. Thus, for example, benzyl and p-nitrobenzyl groups may be removed by hydrogenolysis and t-butyl groups may, for example, be removed by acidolysis or saponification.

Amine protecting groups and carboxyl protecting groups may, for example, be removed simultaneously by acidolysis, alkaline hydrolysis, hydrogenolysis, treatment with sodium or sodium amide or by enzymatic hydrolysis. Such methods include treatment with hydrogen bromide conveniently in the presence of glacial acetic acid and treatment with an alcohol conveniently containing dissolved dry hydrogen chloride.

One method of deprotection is, for example, catalytic hydrogenation, conveniently using palladium on for example carbon as the catalyst and conveniently in the presence of a solvent e.g. water, methanol, dioxan, acetic acid or t-butanol. This method removes, for example, the carbobenzoxy group, but leaves the t-butoxycarbonyl or an acyl group intact.

The reaction product can then be isolated and purified by known methods, such as for example extraction, crystallization or chromatography (e.g. thin layer or column). It may be advantageous to isolate and purify the desired peptide product by salt formation (e.g. hydrochloride, hydrobromide or dicyclohexylamine salt formation). Intermediates and the end products may, for example, be characterized by chromatographic parameters (purity control), optical rotation and possibly spectroscopic data.

According to a still further feature of the present invention there are provided pharmaceutical compositions comprising as active ingredient at least one compound of formula I as hereinbefore defined or a physiologically compatible salt thereof in association with a pharmaceutical carrier or excipient. The compositions according to the invention may be presented, for example, in a form suitable for oral, parenteral or rectal administration.

The term "pharmaceutical" as used herein includes veterinary applications of the invention.

The compounds according to the invention may be presented in the conventional pharmacological forms of administration, such as tablets, coated tablets, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings for example polyvinyl pyrrolidone or shellac, gum arabic, talcum, titanium dioxide or sugar. In order to obtain sustained release or to avoid incompatibilities, the core may consist of several layers too. The table coat may also consist of several layers in order to obtain sustained release, in which case the excipients mentioned above for tablets may be used.

Syrups of the active ingredient according to the invention or combinations of active ingredients may additionally contain a sweetener, such as saccharin, cyclamate, glycerin or sugar, and/or taste improving agents such as flavourings, e.g. vanillin or orange extract. They may also contain suspension agents or thickeners, such as sodium carboxymethyl cellulose, wetting agents, such as for example condensation products of fatty alcohols with ethylene oxide, or preservatives, such as p-hydroxygenzoates.

Injection solutions may, for example, be produced in the conventional manner, such as by the addition of preservation agents, such as p-hydroxybenzoates, or stabilizers, such as Complexons. The solutions are then filled into injection vials or ampoules.

Capsules containing one or several active ingredients may be produced for example by mixing the active ingredients with inert carriers, such as lactose or sorbitol, and filling the mixture into gelatin capsules.

Suitable suppositories may, for example be produced by mixing the active ingredient or active ingredient combinations with the conventional carriers envisaged for this purpose, such as natural fats or polyethyleneglycol or derivatives thereof.

Advantageously, the compositions may be formulated as dosage units, each unit being adapted to supply a fixed dose of active ingredient. Tablets, coated tablets, capsules, suppositories and ampoules are examples of suitable dosage unit forms. Each dosage unit preferably contains 5 to 100 n.mol of the said active ingredient and especially 15 to 50 n.mol of the said active ingredient.

As indicated above, the new compounds may be administered to humans or other animal subjects. The optional dosage is, in general, proportional to surface area and will be in the range 5 to 50 n.mol/m² surface area/day. Thus, for humans having a surface area of the order of 1.5 to 2.0 m², the optional daily dose will be in the range 7.5 to 100 n.mol/day. A course of treatment of 1 to 5 weeks, for example 3 weeks is appropriate. In general, administration is preferably by injection.

According to a still further feature of the present invention there is provided a method of treating obesity caused by overeating which comprises administering an effective amount of a pharmaceutical composition as hereinbefore defined to a patient suffering from such obesity. The peptides may also be used to produce animal models which can be studied and used for therapeutic experiments.

A further major use of the new peptide, however, is in the production of material for immunological assay techniques. The peptide may then be covalently attached to a suitable high molecular carrier such as albumin, polylysine or polyproline in order to be injected into the antibody-producing animal (e.g. rabbits, guinea pigs or goats). High specificity antisera are obtained by use of well known absorption techniques using the high molecular carrier. By introducing radioactivity ($^{14}C$, $^{18}O$, $^{15}N$ etc.) into the peptide molecule, a radioimmuno assay can readily be designed and used for determining the peptide in the different biological fluids such as serum (plasma), urine and cerebrospinal fluid.

In the Example deprotection by catalytic hydrogenation is effected using 10% palladium on carbon as the catalyst. The method of the Example has been chosen so as to avoid side chain protection, thus simplifying the total experimental procedure.

In the Example the following abbreviations are used:

| | |
|---|---|
| DCC | dicyclohexylcarbodiimide |
| DCU | - dicyclohexylurea |
| DME | - dimethoxyethane |
| DMF | - dimethylformamide |
| Gly | - glycyl- |
| His | - L-histidyl- |
| pGlu | - L-(pyro)glutamyl- |
| HOSu | - N-hydroxy succinimide |
| OBzl | - benzyl ester |
| TEA | - triethylamine |
| THF | - tetrahydrofuran |
| p-TosOH | - p-toluene sulphonic acid |
| Z | - carbobenzoxy- |
| i-PrOH | - isopropanol |
| Gel | Silica Gel G |
| S1 | $CH_2Cl_2/MeOH$ (20:3) |
| S2 | MeOH/Benzene (1:1) |
| S4 | $EtOH/H_2O$ (7:3) |
| UV | Ultra violet light - 254 nm |
| N | Ninhydrin |
| CT | chlorine/o-tolidine |
| P | Diazotized sulphanilic acid (Pauly's reagent) |

The solvents used were pro analysi (p.a.) and were treated according to usual laboratory procedures before being used.

SYNTHETIC SCHEME

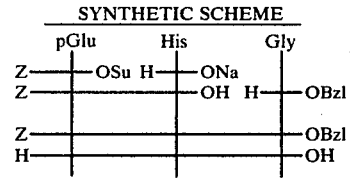

(a) CARBOBENZOXY-L-(PYRO)GLUTAMIC N-HYDROXY-SUCCINIMIDE ESTER (Z-pGlu(OSu))

Z-pGlu(OSu) was synthesized in a similar manner to that described in P. Kurath, A.M. Thomas, Helv. Chim. Acta 56 1656-61 (1973) i.e. in the following manner: Z-Glu(OH) (15 g, 57 mmoles) and HOSu (7.25 g, 63 mmoles) were dissolved in DME (50 ml) and the solution was chilled to −20° C. (in $CCl_4/CO_2$). DCC (13 g, 63 mmoles) in DME (25 ml) was added dropwise to the solution under vigorous stirring. After 2 hrs at −20° C., the temperature was slowly raised to room temperature and stirring was continued overnight. The precipitated DCU was filtered off and the solvent was evaporated in vacuo. The residue was crystallized from i-PrOH, yielding 14 g (70%, litt. 76%) of the product with m.p. 130° C. (litt. 130°–131° C.). $R_f$(Sl) 0.70–0.76.

(B) CARBOBENZOXY-L-(PYRO)GLUTAMYL-HISTIDINE (Z-pGlu-His(OH))

Z-pGlu-His(OH) was synthesized in the following manner:

Z-Glu(OSu) (5.4 g, 15 mmoles) was dissolved in dioxan (25 ml) and added to a solution of His (2.56 g, 16.5 mmoles) and Na$_2$CO$_3$.10 H$_2$O (4.72 g, 16.5 mmoles) in H$_2$O (20 ml) at 0° C. After stirring for 2 hrs at room temperature, the active ester had reacted completely (followed by TLC). The mixture was concentrated to half of its volume in vacuo, chilled to 0° C., and 3 M HCl (5.5 ml) was added under vigorous stirring. The precipitated voluminous material was filtered off, washed with H$_2$O and crystallized from MeOH/H$_2$O (2:5). Yield 3.5 g (60%, litt. 62%), decomp. 140°–160° C., R$_f$ S4) 0.45.

(c) CARBOBENZOXY-L-(PYRO)GLUTAMYL-L-HISTIDYL-GLYCINE BENZYL ESTER (Z-pGlu-His-Gly(OBzl))

Gly (OBzl).pTos(OH) was synthesized in a similar manner to that described in L. Zervas, M. Winitz, J. P. Greenstein J.O.C. 22, 1515–21 (1957). Thus TEA (77 μl, 0.5 mmoles) was added to Z-pGlu-His(OH) (203 mg, 0.5 mmoles) and Gly(OBzl).pTos(OH) (186 mg, 0.5 mmoles) in DMF (5 ml) at 0° C.

DCC (133 mg, 0.55 mmoles) in DMF (2 ml) was then added to the mixture, the temperature was slowly raised to room temperature, and the mixture was stirred overnight. The precipitated DCU was filtered off, and after evaporation of the solvent in vacuo, the residue was dissolved in H$_2$O (5 ml) and the mixture was extracted with CH$_2$Cl$_2$ (3×2 ml). After evaporation of the organic solvent, the crude product (R$_f$ (S1) 0.25; UV+, CT+, P+) was used without further purification in the next step.

(d) L-(PYRO)GLUTAMYL-L-HISTIDYL-GLYCINE (pGlu-His-Gly(OH))

The crude product of Z-pGlu-His-Gly(OBzl) was dissolved in THF/H$_2$O (1:1, 20 ml), Pd/C (100 mg) was added and H$_2$ gas was bubbled through the solution at normal pressure for 1 hr. The reaction was followed on TLC, which showed that a more polar product was being formed. After the reaction was completed, the catalyst was filtered off and the solvent was evaporated in vacuo, leaving a residue that was dissolved in H$_2$O. The aqueous phase was extracted with CH$_2$Cl$_2$ (3×2 ml), thus removing less polar biproducts. The crude product was purified by column chromatography with Silica Gel KG 60 70–230 mesh) and EtOH/H$_2$O (7:3) as the eluting solvent. The yield of chromatographically pure product was 104 mg (64%). R$_f$(S4) 0.45.

The synthetic peptide thus obtained has been shown to be identical in a number of chromatographic systems to the biogenic material which has been isolated from urine as hereinbefore described. The synthetic peptide also has been found to possess comparable biological activity.

The following Pharmaceutical Examples are given by way of illustration only. The term "Peptide" refers to the peptide of formula (I) herein.

EXAMPLE A

Preparations for subcutaneous injection

Freeze-dried Peptide is filled into vials at two different concentrations.

Each vial contains:

| Peptide | 0.05 mg or 0.10 mg |
|---|---|

| -continued | |
|---|---|
| Glycine | 5.0 mg |

The contents of each vial are dissolved in 1 ml of isotonic sodium chloride for injection, prior to use.

EXAMPLE B

Tablets

Each table contains:

| Peptide | 0.1 mg |
|---|---|
| Maize starch | 24.0 mg |
| Lactose | 80.0 mg |
| Gelatin | 1.4 mg |
| Talc | 6.0 mg |
| Magnesium stearate | 0.6 mg |

EXAMPLE C

Nasal drop solution or spray

Each 1.0 ml of solution contains:

| Peptide | 0.5 mg or 1.0 mg |
|---|---|
| Sodium chloride | 4.6 mg |
| NaH$_2$PO$_4$, 2H$_2$O | 4.2 mg |
| Na$_2$ H PO$_4$ . 12 H$_2$O | 14.3 mg |
| Benzalkonium chloride | 0.125 mg |
| Sterile water ad | 1.0 ml |

1 Dose i.e. 2–3 drops (or equivalent spray) contains 0.05 mg or 0.10 mg Peptide.

EXAMPLE D

Suppositories

Each suppository contains:

| Peptide | 0.1 mg or 0.2 mg |
|---|---|
| Adeps solidus (Witepsol H. 15) | 1.8 g |

EXAMPLE E

Suppositories

Each suppository contains:

| Peptide | 0.1 mg or 0.2 mg |
|---|---|
| Polyethylene glycol 1500 | 1.2 g or 1.1 g |
| Polyethylene glycol 3000 | 0.5 g |
| Distilled water | 100.0 mg |

EXAMPLE F

Rectal solution

Content per rectiole:

| Peptide | 0.1 mg or 0.2 mg |
|---|---|
| Phenyl carbinol | 15.0 mg |
| Methyl cellulose | 40.0 mg |
| Sterile water ad | 2.0 ml |

We claim:
1. The compound of the formula:

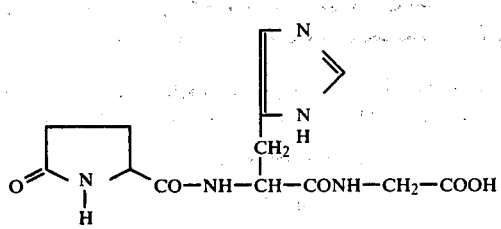

(wherein the pyroglutamyl and histidyl moieties are of the L-series) and salts thereof.

2. The compound as claimed in claim 1 in the form of a physiologically compatible salt.

3. A pharmaceutical anorexigenic composition comprising as active ingredient an anorexigenically effective amount of the compound of formula I as defined in claim 1 or a physiologically compatible salt thereof in association with a pharmaceutical carrier or excipient.

4. A composition as claimed in claim 3 in the form of tablets, coated tablets, emulsions, powders, capsules, syrups, injection solutions or suppositories.

5. A composition as claimed in claim 3 or claim 4 in the form of dosage units wherein each dosage unit contains from 5 to 100 n.mols of the active ingredient.

6. A composition as claimed in claim 5 wherein each dosage unit contains from 15 to 50 n.mols of the active ingredient.

7. A method of treating obesity caused by overeating which comprises administering an effective amount of a pharmaceutical composition as defined in claim 3 to a patient suffering from such obesity.

8. A biochemical agent for use in immunological assay techniques comprising the compound of formula I as defined in claim 1 covalently attached to a high molecular carrier.

9. The biochemical agent as defined in claim 8 wherein the high molecular carrier is albumin, polylysine or polyproline.

* * * * *